United States Patent [19]
Hajos et al.

[11] Patent Number: 5,215,987
[45] Date of Patent: Jun. 1, 1993

[54] SUBSTITUTED BENZHYDRYL 2-HYDROXYPROPYL PIPERAZINE DERIVATIVES

[75] Inventors: Zoltan G. Hajos, Princeton; Ramesh M. Kanojia, Somerville; Jeffrey B. Press, Rocky Hill, all of N.J.

[73] Assignee: Ortho Pharmaceutical Corporation, Raritan, N.J.

[21] Appl. No.: 512,715

[22] Filed: Apr. 23, 1990

[51] Int. Cl.[5] ............... A61K 31/535; A61K 31/495; C07D 403/00; C07D 401/00
[52] U.S. Cl. .................... 514/230.5; 514/252; 514/253; 514/255; 544/105; 544/280; 544/295; 544/360; 544/362; 544/369; 544/364; 544/373; 544/376; 544/396
[58] Field of Search ............ 514/230.5, 252, 253, 514/255; 544/105, 280, 295, 360, 362, 368, 373, 376, 396, 369, 364

[56] References Cited

U.S. PATENT DOCUMENTS

| | | | |
|---|---|---|---|
| 4,361,562 | 11/1982 | Berthold | 514/253 |
| 4,510,140 | 4/1985 | Nardi et al. | 544/360 |
| 4,789,675 | 12/1988 | Meguro et al. | 514/229.8 |
| 4,849,423 | 7/1989 | Ott | 514/253 |
| 4,876,257 | 10/1989 | Hajos et al. | 514/253 |

Primary Examiner—Mukund J. Shah
Assistant Examiner—Matthew V. Grumbling

[57] ABSTRACT

Substituted benzhydryl 2-hydroxypropyl piperazine derivatives and methods of synthesis of the derivatives are described. The substituted benzhydryl 2-hydroxypropyl piperazine derivatives are useful as cardiotonic agents.

21 Claims, No Drawings

SUBSTITUTED BENZHYDRYL 2-HYDROXYPROPYL PIPERAZINE DERIVATIVES

BACKGROUND OF THE INVENTION

1. Field of the Invention

The present invention relates to compounds of the formula:

as further defined herein. The compounds are useful as cardiovascular agents. The compounds possess positive ionotropic activity and are especially useful as cardiotonic agents for improving cardiac ejection, particularly in the setting of acute or chronic congestive heart failure 2. Description of the Prior Art British Patent Application No. GB2186573 and German Patent Application No. DE3703633 relate to purine derivatives possessing cardiotonic and antiarrhythmic activity and having the following formula:

wherein R is an optionally substituted diphenylalkyl group. The side chain in the above formula is bonded to a ring nitrogen atom.

U.S. Pat. No. 4,460,586 relates to 3-aminopropoxyaryl derivatives of the formula:

These compounds are useful as cardiotonic, antiarrhythmic and α- and β-adrenoceptor blocking agents. This United States patent is one of a series of patents that have issued claiming various 4-substituted indole derivatives.

U.S. Pat. No. 4,885,300 relates to 4-substituted pyrazolo pyrimidine derivatives of the formula:

These compounds are useful as cardiotonic and antiarrhythmic agents.

U.S. Pat. No. 4,876,257 relates to 6-substituted purinyl piperazine derivatives of the formula:

These compounds are also useful as cardiotonic and antiarrhythmic agents.

SUMMARY OF THE INVENTION

The present invention is directed to substituted-benzhydryl-2-hydroxypropyl piperazine derivatives of the general formula:

wherein
R is hydrogen or acetyl;
$Ar_1$ and $Ar_2$ are independently phenyl or substituted phenyl wherein the substituent on the phenyl ring is $C_1$-$C_4$ alkyl, $C_1$-$C_4$ alkoxy, trifluoromethyl or halogen; and
X is selected from the group consisting of -continued

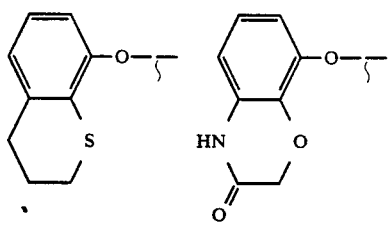

wherein
Y is a mono or disubstituent selected from hydrogen, halogen, amino, $C_1$-$C_4$ alkylamino, $C_2$-$C_4$ alkanoylamino or $C_1$-$C_4$ alkoxy wherein the substituents are the same or different; and $R_1$ is hydrogen, methyl or benzyl.

Also included are optically active isomers of the substituted benzhydryl 2-hydroxypropyl piperazine derivatives.

The compounds of the general formula are useful as cardiovascular agents, and in particular as cardiotonic agents.

DETAILED DESCRIPTION OF THE INVENTION

The invention in its broadest aspects relates to substituted benzhydryl 2-hydroxypropyl piperazine derivatives which exhibit positive ionotropic activity.

The compounds of the present invention can be prepared as outlined in Scheme 1, below.

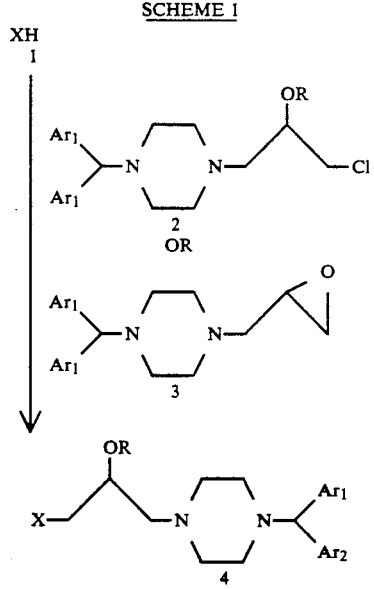

In this case, the appropriately substituted starting compound 1 is treated with a base such as an amine (for example, triethylamine), a metal hydroxide (for example, sodium or potassium hydroxide), a metal hydride (for example, sodium hydride) in an inert solvent such as dimethylformamide (DMF), dimethylsulfoxide (DMSO) or tetrahydrofuran (THF). The anion so formed is reacted with appropriately substituted alkylating agents such as the chloride 2 or the epoxide 3 and the reactants are allowed to react for about 2 to 200 hours at a temperature of about 0° to about 100° C. to form the compounds of the invention 4. The chlorides 2 and epoxides 3 used as the alkylating agents are either commercially available or they can be prepared by procedures found in the chemical literature and available to those skilled in the art.

The compounds of the present invention can also be prepared as described in Scheme 2.

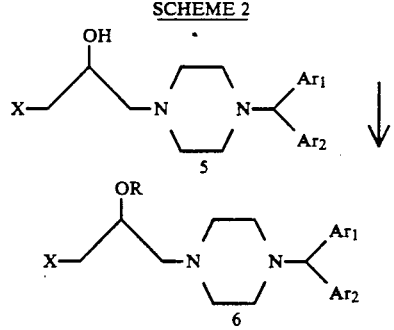

In Scheme 2, an appropriately substituted alcohol 5 is reacted with acetic anhydride in a suitable solvent such as THF or methylene chloride, for example, to form the ester derivative 6.

Alternately, the compounds of the present invention can be prepared as outlined in Scheme 3 where an appropriately substituted racemic or optically active glycidyl derivative 7 is treated with an appropriately substituted benzhydryl piperazine 8 either neat or in the presence of a solvent at a temperature of about 15°-50° C. for from about several hours to several weeks. The resulting product is the piperazine derivative 9 in the racemic or optically active form. Suitable solvents that can be employed in the reaction include methanol, ethanol, DMF and DMSO. The benzhydryl piperazine compounds 8 are available commercially or they can be prepared according to literature procedures known to those skilled in the art.

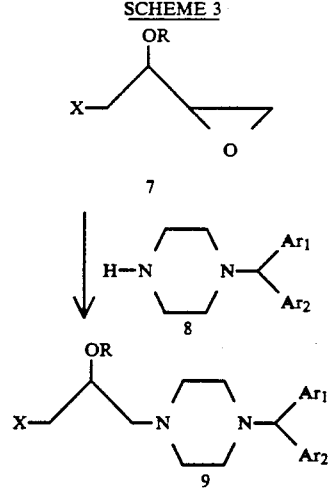

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed, such as, for example, water, glycol, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included; injectable suspensions may also be prepared, in which case appropriate liquid carriers, suspending agents and the like may be employed. The pharmaceutical compositions will generally contain a dosage unit, e.g., tablet, capsule, powder, injection, teaspoonful and the like, from about 0.01 to about 50 mg/kg, and preferably from about 0.1 to about 10 mg/kg of the active ingredient.

The following examples describe the invention in greater particularity and are intended to be a way of illustrating but not limiting the invention. Some of the compounds in the examples were obtained as the hydrate. The water can be removed from the hydrates by drying at temperatures below the melting point of the compound.

EXAMPLE 1

5-Acetamido-4-amino-6-[1-[1-[bis(4-fluorophenyl)methyl]-piperazin-4-yl]-2-acetoxy -3-propanylthio]pyrimidine Hydrate To 4,5-diamino-6-[1-[1-[bis(4-fluorophenyl-)methyl]-piperazin-4-yl]2-hydroxy-3-propanylthio]pyrimidine (1.0 g, 2.0 mmol) was added an excess of acetic acid (11 mL). The mixture was heated to 80° C. for 3 days and then heated to reflux for 4 days. The acetic acid was removed in vacuo and the residue purified through silica gel (10% methanol:methylene chloride) to give the pure product (320 mg, 31.4%) as a brown solid; mp. 79°–81° C. (dec.); DCI/MS (M+1)=571. (300 MHz) $^1$H NMR (CDCl$_3$)δ: 8.2 (s,1H); 7.3 (m,4H); 6.9 (m,4H); 5.2 (m, 1H); 4.2 (s,1H); 3.2–3.75 (q of q,2H); 2.5 (m,10H); 2.2 (s,3H); 2.0 (s,3H).

Calc for $C_{28}H_{32}F_2N_6O_3S \cdot H_2O$: C,58.02; H,5.74; N 14.50.

Found: C,58.02; H,5.55; N,14.67.

EXAMPLE 2

2-[1-[1-[Bis(4-fluorophenyl)methyl]piperazin-4-yl]-2-hydroxy-3-propanylthio]pyridine Hemihydrate To NaH (10 mmol, 0.48 g, pentane washed) in DMF (10 mL) was added 2-mercaptopyridine (10 mmol, 1.11 g) at 0° C. After stirring for 2 hours at 0° C., 1-(1-chloro-2-hydroxy-3-propanyl)-4-(4, 4'-difluorobenzhydryl)piperazine (5 mmol, 1.91 g) in DMF (20 mL) was added dropwise under nitrogen over 10 minutes. The mixture was stirred 15 minutes at 0° C. and 5 days at room temperature. The mixture was then filtered and the filtrate concentrated in vacuo (1 mmHg, 70° C.). The concentrated mixture was purified on a silica gel column using 5% methanol:methylene chloride. Crude material thus obtained was rechromatographed on silica gel using 10% acetone:methylene chloride and then 10% methanol:methylene chloride. After drying in a vacuum dessicator overnight, the pure product was an amber glass (0.87 g, 38.1%); DCI MS (M+1)=456; (300 MHz) $^1$H NMR (CDCl$_3$)δ:8.4 (d,1H) and 7.5 (m,1H), 7.3 (m,4H), 7.25 (m,1H), 7.0 (m,5H), 4.0 (m, 1H), 3.2–3.6 (m,4H), 2.5 (m,10H).

Calc for $C_{25}H_{27}F_2N_3OS \cdot \frac{1}{2}H_2O$: C,64.63; H,6.07; N 9.04.

Found: C,64.70; H,5.98; N, 8.50.

EXAMPLE 3

4-[1-[1-[Bis(4-fluorophenyl)methyl]piperazin-4-yl]-2-acetoxy-3-propanylthio]pyridine To 4-mercaptopyridine (0.555 g, 5 mmol) in DMF Hemihydrate To 4-mercaptopyridine (0.555 g, 5 mmol) in DMF (5 mL) with triethylamine (0.7 mL, 5 mmol) was added 1-(1-chloro-2-hydroxy-3-propanyl)-4-(4, 4'-difluorobenzhydryl) piperazine (1.91 g, 5 mmol) in DMF (15 mL) dropwise over 15 minutes under nitrogen. After 8 days, the reaction mixture was heated to 60° C. and stirred for 3 days. The DMF was removed in vacuo (1 mmHg, 60° C.) and to this crude material was added methylene chloride (5 mL), acetic anhydride (5 mmol, 0.47 mL) and triethylamine (5 mmol, 0.7 mL), and the mixture was stirred overnight. Silica gel flash chromatography using 10% methanol:methylene chloride gave an amber oil which was dissolved in methylene chloride (10 mL) and extracted with saturated sodium bicarbonate (2×20 mL), water (1×20 mL), saturated brine (1×20 mL) and dried over sodium sulfate. The solvent was removed in vacuo to give pure product (0.38 g, 15.3%); DCI/MS (M+1)= 498; 300 MHz $^1$H NMR (CDCl$_3$)δ: 8.4(d,2H,J=1.25 Hz), 7.3 (m,4H), 7.2 (d,2H,J=1.4 Hz), 6.95 (m, 4H), 5.1 (m, 1H), 4.2 (s, 1H), 3.3 and 3.2 (d of d and d of d, 2H), 2.6 (d, 2H,J=6.1 Hz), 2.35 (m, 8H), 2.0 (s,3H).

Calc for $C_{27}H_{29}F_2N_3O_2S \cdot \frac{1}{2} H_2O$: C, 64.01; H, 5.97; N, 8.29.

Found: C, 63.95; H, 5.77; N, 7.80

EXAMPLE 4

2-[1-[1-[Bis(4-fluorophenyl)methyl]-piperazin-4-yl]-2-hydroxy-3-propanylthio] -benzothiazole Monomalonate Dihydrate To ethanol (10 mL) was added 2-mercaptobenzothiazole (5 mmol, 836 mg), triethylamine (5 mmol, 0.7 mL) and then 1-(1-chloro-2-hydroxy-3-propanyl)-4-(4,4'-difluorobenzhydryl)piperazine (5mmol, 1.9 g) in ethanol (40 mL) dropwise over 40 minutes under nitrogen. After 10 days the ethanol was removed in vacuo to give a brown oil. Silica gel flash column chromography gave pure product as an amber oil (1.81 g, 70.7%). To this oil (1.5 g, 2.93 mmol) in methanol (5 mL), was added malonic acid (305 mg, 2.93 mmol) in methanol. After 4 hours, the methanol was removed in vacuo to give pure product (1.68 g, 93.1%); mp 58°–61° C.; DCI/MS (M+1)=512; (400 MHz $^1$H NMR (CDCl$_3$)δ: 8.0 (m, 1H), 7.85 (d of d, 1H), 7.45 (m, 2H), 7.4 (m, 4H), 7.1 (m, 4H), 4.1 (m, 1H), 3.6 and 3.7 (q of q, 2H), 3.05 (s, 2H), 2.6 (m, 10H).

Calc for $C_{27}H_{27}F_2N_3O \cdot C_3H_4O_4 \cdot 2 H_2O$:
C, 55.30; H, 5.41; N, 6.44.

Found: C, 55.34; H, 5.34; N, 6.09.

When in the above procedure, 6-ethoxy-2-mercaptobenzothiazole is used as the starting material in place of 2-mercaptobenzothiazole, 6-ethoxy-2-[1-[1-[bis(4-fluorophenyl) methyl]piperazin-4-yl]-2-hydroxy-3-propanylthio]benzothiazole monomalonate dihydrate is obtained.

Furthermore, when 5-chloro-2-mercaptobenzothiazole is used as the starting material in the above procedure, 5-chloro-2-[1-[1-[bis(4-fluorophenyl)methyl]piperazin-4-yl]-2-hydroxy-3-propanylthio ]benzothiazole monomalonate dihydrate is obtained.

EXAMPLE 5

4,5-Diamino-6-[1-[1-[bis(4-fluorophenyl)-methyl]piperazin-4-yl]-2-hydroxy-3-propanylthio]pyrimidine·¼Hydrate To 4,5-diamino-6-mercaptopyrimidine (25 mmol, 3.55 g) in DMF (30 mL) with triethylamine (25 mmol, 3.5 mL) was added 1-(1-chloro-2-hydroxy-3-propanyl)-4-(4,4'-difluorobenzhydryl)piperazine (25 mmol, 9.55 g) in DMF (45 mL) dropwise over 15 minutes under nitrogen. The mixture was heated at 60° C. for 24 hours and the DMF was removed in vacuo (1 mmHg, 70° C.). The crude product was eluted through silica gel using 10% methanol:methylene chloride. The material thus obtained was dissolved in methylene chloride (50 mL) and washed with water (2×50 mL) and saturated brine (1×50 mL), and dried over sodium sulfate. Concentration in vacuo gave pure product (4.40 g, 36.1%); mp 104°–106° C.; DCI/MS (M+1)= 487; (300 MHz) $^1$H NMR (CDCl$_3$)δ: 8.0 (s, 1H), 7.3 (m, 4H), 7.0 (m, 4H), 4.2 (s, 1H), 4.15 (m, 1H), 3.2 and 3.4 (q of q, 2H), 2.9 (m, 4H), 2.8 (m, 2H), 2.5 (m, 4H).

Calc for $C_{24}H_{28}N_6F_2OS·¼ H_2O$: C, 58.69; H, 5.85; N, 17.11.

Found: C, 58.44; H, 5.64; N, 16.54.

When in the above procedure, 4,6-diamino-2-mercaptopyrimidine is used as the starting material in place of 4,5-diamino-6-mercaptopyrimidine,4,6-diamino-2-[1-[1-[bis(4-fluorophenyl)methyl] piperazin-4-yl]-2-hydroxy-3-propanylthio]pyrimidine·¼ hydrate is obtained.

EXAMPLE 6

1-[1-[1-(Bis(4-fluorophenyl)methyl]-piperazin-4-yl]-2-hydroxy-3-propanyl]-2,3,6,7-tetrahydro-3,7-dimethyl-2,6-dioxo-1H-purine To sodium hydride (0.3 g, 6.25 mmol of 50% with oil, prewashed with pentane) was added dry dimethyl sulfoxide (12 mL) and theobromine (0.9 g, 5 mmol). A fine suspension was formed to which was added 1-(1-chloro-2-hydroxy-3-propanyl)-4-(4, 4'-difluorobenzhydryl)piperazine (1.9 g, 5 mmol) dissolved in dry DMSO (10 mL) over 5 minutes. The mixture was stirred at room temperature under nitrogen for 24 hours and then heated to 70° C. for 20 hours. The DMSO was evaporated in vacuo (1 mmHg) at 75° C. and the residue was triturated in methylene chloride and filtered through Celite®. The filtrate was evaporated in vacuo to give a tacky solid (2.62 g) which was purified by flash chromatography over silica gel using 10% methanol/methylene chloride to give the desired product which was further purified with ether. The ether insoluble material was pure product (0.6 g, 25%), mp 138°–140° C.; DCI/MS: 525; 100 MHz $^1$H NMR (CDCl$_3$)δ: 7.85 (s, 1H), 7.32 (m, 4H), 6.95 (m, 4H), 4.2 (s, IH), 4.1–4.22 (m, 3H), 3.97 (s, 3H), 3.57 (s, 3H), 2.3–2.5 (m, 10H).

Calc for $C_{27}H_{30}F_2N_6O_3$: C, 61.82; H, 5.76; N, 16.02.
Found: C, 61.71; H, 5.81; N, 15.85.

EXAMPLE 7

2-[1-[1-[Bis (4-fluorophenyl)-methyl] piperazin-4-yl]-2-hydroxy-3-propanylthio]pyrimidine To NaH (240 mg, 5 mmol, 50% in oil, prewashed with pentane) in DMF (5 mL) was added 2-mercaptopyrimidine (5 mmol, 560 mg) in portions over 5 minutes at 0° C. After 30 minutes, 1-(1-chloro-2-hydroxy-3-propanyl)-4-(4,4'-diflurobenzhydryl)piperazine (1.9 g, 5 mmol) in DMF (15 mL) was added over 10 minutes under nitrogen. After 12 days, the sodium chloride was removed by filtration and the DMF was removed in vacuo (~0.5 mm Hg, ~50° C.) to give the crude (1.82 g). Flash column chromatography over silica gel using 2% methanol:methylene chloride (2×) and subsequent washings of the product with pentane gave the pure product (380 mg, 16.7%) as a white solid, mp 75°–76° C.; DCI/MS (M+1)=456; (400 MHz) $^1$H NMR (CDCl$_3$)δ: 8.55 (s, 1H), 8.50 (s,1H), 7.35 (m, 4H), 7.0 (m, 4H), 4.2 (s, 1H) , 4.0 (m, 1H), 3.3 (m, 2H), 2.65 (m, 2H), 2.4 (m, 8H).

Calc for $C_{24}H_{26}F_2N_4OS$: C, 63.26; H, 5.75; N, 12.29.
Found: C, 62.97; H, 5.87; N, 11.91.

EXAMPLE 8

2-(3-Indolyl)-2-[1-[1-bis(4-fluorophenyl)-methyl]-piperazin-4-yl]-2-hydroxy-3 -propyl]acetonitrile ½hydrate To sodium hydride (300 mg, 50% in mineral oil prewashed with pentane, 6.25 mmol) was added pentane (10 mL). After stirring under nitrogen for 5 minutes, the pentane was decanted, dry DMF (12 mL) was added and the mixture was cooled in an ice bath to 0° C. 3-Indolyl acetonitrile (780 mg, 5 mmol) was then added in DMF (7.5 mL) over a period of 15 minutes. After stirring for an additional 1 hour at 0° C., 1-(1-chloro-2-hydroxy-3-propanyl)-4-[bis(4-fluorophenyl) methyl]-piperazine (1.9 g, 5 mmol) dissolved in DMF (7.5 mL) was added under nitrogen over a period of 10 minutes. The mixture was allowed to come to room temperature and was stirred under nitrogen at room temperature for 7 days. The solvent was evaporated in vacuo (1 mm Hg, 50° C.); the residue was dispersed in methylene chloride, filtered through Celite®, and the filtrate was evaporated vacuo to give the crude reaction product (2.5 g). Purification by flash column chromatography using silica gel (140 g) and methylene chloride eluent gave 1.1 g in the slowest fractions which was rechromatographed over silica gel (60 g) using 5% methanol-methylene chloride eluent to give the title compound (230 mg), mp 79°–81° C. (dec), as a light beige powder; 300 MHz $^1$H-NMR (CDCl$_3$)δ: 7.58 (d, 1H), 7.2–7.4 (m, 8H), 6.95 (m, 4H), 4.2 (s, 1H), 4.15 (m, 1H), 3.8 (m, 3H), 2.3–2.6 (m, 10H); IR (KBr) 2240 cm$^{-1}$; DCI–MS M+1=501.

Calc for $C_{30}H_{30}F_2N_4O·3/4H_2O$: C, 70.09, H, 6.18, N, 10.89.

Found: C, 70.10; H, 6.19; N, 10.68.

EXAMPLE 9

1-[1-[1[Bis(4-fluorophenyl)methyl]-piperazin-4-yl]-2-hydroxy-3-propanylthio ]naphthalene·½H$_2$O To sodium hydride (500 mg, 50% in mineral oil prewashed with pentane, 10 mmol) was added pentane (30 mL). After stirring under nitrogen for 5 minutes, the pentane was decanted, and dry DMF (12 mL) was added. It was cooled in an ice bath to 0° C., and naphthalene-1-thiol (1.4 mL, 1.6 g, 10 mmol) was added in DMF (10 mL) over a period of 15 minutes. To the resulting greenish-yellow fine suspension was added 1-(1-chloro-2-hydroxy-3-propanyl)-4-[bis(4-fluorophenyl) methyl]piperazine (3.8 g, 10 mmol) dissolved in DMF (20 mL) under nitrogen over a period of 10 minutes at 0° C. The mixture was allowed to come to room temperature and stirred under nitrogen for 5 days, and the solvent was evaporated in vacuo (1 mm Hg, 50° C.). The resulting oil (4.8 g) was purified by flash column chromatography over silica gel using methylene chloride eluent. The first eluate gave a solid (1.0 g) which was identified as bis(1-naphthyl)disulfide. The second eluate (using 10% methanol-methylene chloride) gave the title compound (2.0 g), mp 50°-52° C., as a light-beige powder; 300 MHz $^1$H-NMR (CDCl$_3$)δ: 8.41 (d, J=8Hz, 1H), 7.37-7.85 (m, 6H), 6.93-7.37 (m, 8H), 4.19 (s, 1H), 3.82 (m, 1H), 3.81 (m, 2H), 2.3-2.8 (m, 10H); DCI-MS (M+1)=505.

Calc for $C_{30}H_{30}F_2N_2OS \cdot \frac{1}{3}H_2O$: C, 70.56, H, 6.05; N, 5.49.

Found: C, 70.49; H, 5.98; H 5.95.

EXAMPLE 10

1-Benzyl-5-[4-[bis(4-fluorophenyl)methyl]-piperazin-1-yl]-2-hydroxy..3-propanyl]-1 H-pyrrolo[3,2-c1pyridino-4(5H)-one Sodium hydroxide (0.088 g, 2.2 mmol) was added to a solution of 1-benzyl-4,5-dihydro-4-oxo-5-azaindole (0.5 g, 2.2 mmol) in DMF (20 mL). After the mixture was stirred for 15 minutes, 1-(1-chloro-2-hydroxy-3-propanyl)-4-[bis(4-fluorophenyl)methyl]piperazine (0.844 g, 2.2 mmol) was added and the mixture was stirred at room temperature for 18 hours. The solvent was removed in vacuo, the residue was dissolved in methylene chloride and the solution washed with water and saturated brine and dried over sodium sulfate. The solid thus obtained (0.32 g, 26%) was purified on silica gel using 5% methanol in methylene chloride to give the title compound as a beige solid, mp 86°-88° C.; MS (DCI) 569 M+H; IR (KBr) 2937, 1637, 1562, 1512, 1450, 1394, 1225 cm$^{-1}$; 400 MHz $^1$H NMR (CDCl$_3$)δ: 7.34-6.88 (m, 16H), 6.25 (d, 1H), 4.37 (d, 1H), 4.18 (s, 1H), 4.05 (brs, 1H), 3.88-3.10 (m, 1H), 2.65-2.6 (m, 13H).

Calc for $C_{34}H_{34}F_2N_4O_2$: C, 71.81; H, 6.02; N, 9.85.
Found: C, 71.58; H, 5.96; N, 9.83.

EXAMPLE 11

8-[3-[4-(Diphenylmethyl)piperazin-1-yl]-2-hydroxypropoxy]-3,4-dihydro-2H, 1-benzothiopyran A mixture of 8-(2,3-epoxypropoxy)-3,4-dihydro-4H-benzothiopyran (0.45 g, 2.024 mmol) and 1-diphenyl)-methylpiperazine (0.612 g, 2.43 mmol) in methanol (15 mL) was heated to reflux under nitrogen for hours. The solvent was removed in vacuo and the residue dissolved in methylene chloride which was reevaporated. The residue was purified using silica gel flash chromatography with 3% methanol in methylene chloride to give the title compound as a colorless foam, 0.96 g (100%), mp 68°-70° C.; IR (KBr) 3400, 1569, 1447, 1256 cm$^{-1}$; 300 MHz $^1$H NMR (CDCl$_3$)δ: 2.07 (m, 2H), 2.2-3.08 (m, 12H), 3.9-4.2 (m, 5H), 4.22 (s, 1H), 6.6-7.6 (m, 13H); MS (DCI) 475 (MH)+.

Calc for $C_{29}H_{34}N_2O_2S$: C, 73.38; H, 7.22; N, 5.90.

Found: C, 73.29; H, 7.15; N, 5.90.

EXAMPLE 12

8-[3-[4-(Diphenylmethyl)piperazin-1-yl]-2-hydroxypropoxy]-2,3-dihydro-4H-benz5,6]oxazin-3-one·¼ Hydrate A mixture of 8-(2,3-epoxy)-2,3-dihydro-4H-benz[5,6]oxazin-3-one (0.442 g, 2 mmol) and 1-(diphenyl)methylpiperazine (0.505 g, 2 mmol) in methanol (5 mL) was heated to reflux for 2 hours under nitrogen. The solvent was removed in vacuo and the residue was purified using flash chromatography on silica gel using 5% methanol in methylene chloride to give the title compound as a colorless foam, 0.86 g (90%). Recrystallization from methanol/ether gave the analytical product, mp 160°-162°-C.; IR (KBr) 1690 cm$^{-1}$; 300 Mc $^1$H NMR (CDCl$_3$)δ: 2.0-2.8 (m, 6H), 4.02 (s, 1H), 4.22 (s, 1H), 4.62 (s, 2H), 6.45 (d, 1H), 6.66 (d, 1H), 6.86 (d, 1H), 7.1-7.5 (m, 10H), 8.45 (br s, 1H); MS (DCI) 474 (MH)+.

Calc for $C_{28}H_{31}N_3O_4 \cdot \frac{1}{4} H_2O$: C, 70.34; H, 6.64; N, 8.77.

Found: C, 70.33; H, 6.66; N, 8.81.

EXAMPLE 13

Cardiotonic Activity

Adult mongrel dogs were anesthetized with sodium pentobarbital (45 mg/kg, i.p.) and artificially respired by the method of Alousi, A. A. et al. (*Circl. Res.*, 1979, 45, 666). Mean arterial pressure (MAP) was recorded from a cannulated femoral artery and drugs were infused into a cannulated femoral vein. The arterial pressure pulse was used to trigger a cardiotachometer for determination of heart rate (HR). Left ventricular pressure was measured with a Millar catheter and dP/dt$_{max}$ was derived. A right thoracotomy was performed and myocardial contractile force (CF) was measured with a Walton Brodie strain gauge sutured to the right ventricle. The ventricular muscle was stretched to produce a baseline tension of 100 g. A catheter was inserted 2 cm distal to the pyloric valve via a flank incision for intraduodenal (i.d.) drug administration. A standard dose of dopamine (10-15 μg/kg/minute for 3 minutes) was administered to determine myocardial responsiveness to inotropic stimulation.

Example compounds were solubilized in a small volume of DMF diluted to a final concentration of 10% in physiological saline. Alternatively, where possible, a soluble hydrochloride salt was prepared by addition of 0.1N HCl diluted in physiological saline. Vehicles were tested in appropriate volumes and found to exert less than a 5% effect on contractile fore. For i.v. studies, compounds were administered by infusion pump (one drug per animal) at rates of 0.58-2.2 mL/minute in three to four stepwise increasing doses. Each dose was infused over 5 minutes immediately after the effect of the previous dose peaked. For i.d. studies, compounds were injected into the duodenum through an indwelling catheter in a 10 mL bolus. MAP, HR, dP/dt$_{max}$ and CF responses were continuously monitored on a Beckman or Gould recorder and expressed as a percent change from pre-drug control values vs. the cumulative dose of drug administered. For these studies, n of 1 to 5 test animals were used.

Quantitation of the inotropic potency was obtained by calculation of the contractile force (CF) ED$_{50}$. This was defined as the dose of compound that produced a 50% increase above baseline in myocardial contractile force. The value was obtained from three to four point dose-response curves using either graphical estimation (n<3) or linear regression analysis (n≧3). Data from this evaluation are shown in Table 1 below. Numbers in parentheses are the number of animals screened.

TABLE 1

Biological Data For Substituted-Benzhydryl 2-Hydroxypropyl Piperazine Derivatives

| Compound of Example | DOSE (i.v.) | MAP | HR | dP/dt | CF |
|---|---|---|---|---|---|
| 1 | 1.875 (1) | −1 | 12 | 75 | 92 |
| 2 | 1.875 (1) | −6 | −2 | 8 | 28 |
| 3 | 1.875 (1) | 0 | 7 | 31 | 40 |
| 4 | 1.875 (1) | −1 | 9 | 45 | 29 |
| 5 | 1.875 (1) | 4 | 16 | 78 | 55 |
| 6 | 1.875 (1) | 1 | 4 | 28 | 32 |
| 7 | 1.875 (2) | −10 | −10 | 65 | 112 |
| 8 | 1.875 (1) | −4 | −1 | 45 | 51 |
| 9 | 1.875 (1) | −1 | 6 | 16 | 26 |
| 10 | 1.875 (1) | −8 | 8 | 66 | 78 |
| 11 | 1.875 (2) | 0 | 8 | 36 | 58 |
| 12 | 1.938 (2) | −7 | 6 | 44 | 48 |

What is claimed is:

1. A compound of the formula $$X-CH_2-CHOR-CH_2-N(\text{piperazine})N-CH(Ar_1)(Ar_2)$$

wherein
R is hydrogen or acetyl;
Ar₁ and Ar₂ are independently phenyl or substituted phenyl wherein the substituent on the phenyl ring is $C_1-C_4$ alkyl, $C_1-C_4$ alkoxy, trifluoromethyl or halogen;
X is selected from the group consisting of

[structures of Y-substituted pyrimidinylthio, pyridinylthio, pyrazinylthio, pyridinylthio, benzothiazolylthio, naphthylthio, pyrrolopyridinyl, indolyl(CN), chromanyloxy, and acetamidophenoxy groups]

wherein
Y is a mono or disubstituent selected from hydrogen, halogen, amino, $C_1-C_4$ alkylamino, $C_2-C_4$ alkanoylamino or $C_1-C_4$ alkoxy wherein the substituents are the same or different; and
R₁ is hydrogen, methyl or benzyl.

2. The compound of claim 1 wherein Ar₁ and Ar₂ are substituted phenyl.

3. The compound of claim 2 wherein Ar₁ and Ar₂ are substituted phenyl, substituted with a halogen.

4. The compound of claim 3 wherein Ar₁ and Ar₂ are substituted phenyl, substituted with a fluoro group.

5. The compound of claim 1 selected from the group consisting of 5-acetamido-4-amino-6-[1-[1-[bis(4-fluorophenyl) methyl]-piperazin-4-yl]-2-acetoxy-3-propanylthio]pyrimidine hemihydrate; 2-[1-[1-[bis(4-fluorophenyl)methyl]piperazin-4-yl]-2-hydroxy-3-propanylthio]pyridine; 4-[1-[1-[bis(4-fluorophenyl)methyl]piperazin-4-yl]-2-acetoxy-3propanylthio]pyridine hemihydrate; 2-[1-[1-[bis(4-fluorophenyl)methyl]piperazine-4-yl]-2-hydroxy-3-propanylthio ]benzothiazole monomalonate dihydrate; 4,5-diamino-6-[1[1[bis(4-fluorophenyl)methyl]-piperazin-4-yl]-2-hydroxy-3-propanylthio]-pyrimidine·¼ hydrate; 2-[1-[1-[bis(4-fluorophenyl)methyl] piperazin-4-yl]-2-hydroxy- 3propanylthio]pyrimidine; and 1-[1-[1[bis(4fluorophenyl)methyl]piperazin-4-yl]-2-hydroxy-3-propanylthio] naphthalene·½H₂O.

6. The compound of claim 2 selected from the group consisting of 2-(3-indolyl)-2-[1-[1-bis(4-fluorophenyl)-methyl]-piperazin-4-yl]-2-hydroxy-3-propyl]acetonitrile; and 1-benzyl-5-[4-[bis(4-fluorophenyl)methyl]-piperazin-1-yl]-2-hydroxy-3-propanyl]-1 H-pyrrolo[3,2-c]pyridino-4(5H)-one.

7. The compounds of claim 1 selected from the group consisting of 8-[3-[4-(diphenylmethyl)piperazin-1-yl]-2-hydroxypropoxyl-3,4-dihydro-2H,1benzothiopyran and 8-[3-[4-(diphenylmethyl)-piperazin-1-yl]-2-hydroxypropoxy]-2,3-dihydro-4H-benz[5, 6]oxazin-3-one·¼ hydrate.

8. A pharmaceutical composition comprising as an active ingredient an effective amount of the compound of claim 1, and a suitable pharmaceutical carrier.

9. A pharmaceutical composition comprising as an active ingredient an effective amount of the compound of claim 2, and a suitable pharmaceutical carrier.

10. A pharmaceutical composition comprising as an active ingredient an effective amount of the compound of claim 3, and a suitable pharmaceutical carrier.

11. A pharmaceutical composition comprising as an active ingredient an effective amount of the compound of claim 4, and a suitable pharmaceutical carrier.

12. A pharmaceutical composition comprising as an active ingredient an effective amount of the compound of claim 5, and a suitable pharmaceutical carrier.

13. A pharmaceutical composition comprising as an active ingredient an effective amount of the compound of claim 6, and a suitable pharmaceutical carrier.

14. A pharmaceutical composition comprising as an active ingredient an effective amount of the compound of claim 7, and a suitable pharmaceutical carrier.

15. A method of treating heart disease in mammals by administering an effective amount of the compound of claim 1.

16. A method of treating heart disease in mammals by administering an effective amount of the compound of claim 2.

17. A method of treating heart disease in mammals by administering an effective amount of the compound of claim 3.

18. A method of treating heart disease in mammals by administering an effective amount of the compound of claim 4.

19. A method of treating heart disease in mammals by administering an effective amount of the compound of claim 5.

20. A method of treating heart disease in mammals by administering an effective amount of the compound of claim 6.

21. A method of treating heart disease in mammals by administering an effective amount of the compound of claim 7.

* * * * *